(12) United States Patent
Howard et al.

(10) Patent No.: US 8,795,194 B2
(45) Date of Patent: Aug. 5, 2014

(54) TISSUE HARVESTING (75) Inventors: Mark Howard, East Riding (GB); Mark Smith, Huby (GB)

(73) Assignee: Smith & Nephew, Inc., Memphis, TN (US)

( * ) Notice: Subject to any disclaimer, the term of this patent is extended or adjusted under 35 U.S.C. 154(b) by 904 days.

(21) Appl. No.: 12/058,910

(22) Filed: Mar. 31, 2008

(65) Prior Publication Data

US 2008/0243028 A1    Oct. 2, 2008

Related U.S. Application Data

(60) Provisional application No. 60/909,253, filed on Mar. 30, 2007, provisional application No. 61/006,662, filed on Jan. 25, 2008, provisional application No. 61/006,663, filed on Jan. 25, 2008, provisional application No. 60/992,210, filed on Dec. 4, 2007.

(30) Foreign Application Priority Data

Aug. 8, 2007  (GB) ..................................... 0715429

(51) Int. Cl.
*A61B 10/02* (2006.01)
*A61M 1/00* (2006.01)
*B01D 25/00* (2006.01)

(52) U.S. Cl.
USPC ............ 600/563; 600/565; 604/319; 210/300

(58) Field of Classification Search
USPC .............. 600/562–571; 606/79–81, 167–173; 210/300, 301, 312–313, 321.6, 321.64, 210/321.72, 323.1, 323.2, 335, 433.1; 604/319–321

See application file for complete search history.

(56) References Cited

U.S. PATENT DOCUMENTS

| 3,231,091 | A | * | 1/1966 | Kingsbury et al. ............ 210/335 |
| 5,077,012 | A | * | 12/1991 | Guirguis ........................ 422/401 |
| 5,108,381 | A | * | 4/1992 | Kolozsi ........................ 604/319 |
| 5,607,474 | A | | 3/1997 | Athanasiou et al. |
| 5,804,366 | A | * | 9/1998 | Hu et al. ........................ 435/1.1 |
| 5,876,452 | A | | 3/1999 | Athanasiou et al. |

(Continued)

FOREIGN PATENT DOCUMENTS

DE   3417248 A1   11/1985
EP    669105 A3   1/1996

(Continued)

OTHER PUBLICATIONS

International Search Report and Written Opinion for PCT/US2008/058821 Dated Jul. 18, 2008.

(Continued)

*Primary Examiner* — Max Hindenburg
*Assistant Examiner* — John Pani
(74) *Attorney, Agent, or Firm* — David L. Fox; JL Salazar Law Firm (57) ABSTRACT

The present disclosure relates to a tissue collection apparatus. The tissue collection apparatus comprises a housing defining an inlet and an outlet, a first filter disposed within the housing, a second filter disposed within the housing, the second filter configured to isolate tissue particles of a desired size that pass through the first filter under the application of an aspiration force applied through the housing. A method of harvesting tissue is also disclosed.

8 Claims, 9 Drawing Sheets

(56) References Cited

U.S. PATENT DOCUMENTS

| | | | |
|---|---|---|---|
| 6,013,853 | A | 1/2000 | Athanasiou et al. |
| 6,071,284 | A * | 6/2000 | Fox .................................. 606/80 |
| 6,299,763 | B1 * | 10/2001 | Ashman .......................... 210/94 |
| 7,115,100 | B2 | 10/2006 | McRury et al. |
| 7,611,473 | B2 * | 11/2009 | Boock et al. ................... 600/564 |
| 2002/0161449 | A1 | 10/2002 | Muschler |
| 2003/0114936 | A1 * | 6/2003 | Sherwood et al. ......... 623/23.58 |
| 2003/0130594 | A1 | 7/2003 | Hynes et al. |
| 2004/0078090 | A1 | 4/2004 | Binette et al. |
| 2004/0193071 | A1 | 9/2004 | Binette et al. |
| 2005/0038520 | A1 | 2/2005 | Binette et al. |
| 2005/0059905 | A1 * | 3/2005 | Boock et al. ................... 600/567 |
| 2005/0125077 | A1 | 6/2005 | Harmon et al. |
| 2007/0016100 | A1 | 1/2007 | Miller |

FOREIGN PATENT DOCUMENTS

| | | |
|---|---|---|
| EP | 1378209 A4 | 1/2006 |
| EP | 2139400 B1 | 1/2011 |
| WO | WO9315694 A1 | 8/1993 |
| WO | WO9959500 A2 | 11/1999 |
| WO | WO03073945 A1 | 9/2003 |
| WO | 2005110278 A2 | 11/2005 |
| WO | WO2006098293 A1 | 9/2006 |

OTHER PUBLICATIONS

International Preliminary Report on Patentability for International Application No. PCT/US2008/058821, issued Oct. 6, 2009.

Patent Examination Report No. 1 for Australian Applicatoin No. 2008232516, mailed Jul. 23, 2012.

Communication Pursuant to Article 94(3) EPC for European Application No. 08744717.3, mailed Jan. 26, 2010.

Patent Examination Report No. 1 for Australian Application No. 2008232461, mailed Sep. 12, 2012.

Patent Examination Report No. 2 for Australian Application No. 2008232516, mailed May 21, 2013, 3 pages.

International Search Report for International Application No. PCT/US2008/059624, mailed Jul. 17, 2008.

International Prelimininary Report on Patentability for International Application No. PCT/US2008/059624, issued Oct. 6, 2009.

Notice of Reasons for Rejection for Japanese Application No. 2010-501274, mailed Dec. 11, 2012.

Notice of Reasons for Rejection for Japanese Application No. 2010-501291, mailed Dec. 11, 2012.

English Translation and Notice of Reasons for Rejection for Japanese Patent Application No. 2010-501291 dated Jul. 23, 2013, 7 pages.

* cited by examiner

TISSUE HARVESTING

CROSS-REFERENCE TO RELATED APPLICATIONS

This application claims priority to U.S. Patent Application No. 60/909,253 filed on Mar. 30, 2007, U.S. Patent Application No. 60/992,210 filed on Dec. 4, 2007, U.S. Patent Application No. 61/006,662 filed on Jan. 25, 2008, U.S. Patent Application No. 61/006,663 filed on Jan. 25, 2008, and UK Provisional Patent Application 0715429.7 filed on Aug. 8, 2007, the disclosures of which are incorporated herein by reference in their entirety.

TECHNICAL FIELD

The present disclosure relates to tissue harvesting.

BACKGROUND

Articular cartilage lines the ends of bones and facilitates frictionless movement of joints. Damage to the cartilage caused by injury or disease does not heal and the pathological changes resulting from this damage can be a source of great pain; limiting mobility and having a significant detrimental impact on the quality of life. Over time, lesions are likely to degenerate into osteoarthritis. Injury is not the only cause of osteoarthritis, with genetics, obesity, joint biomechanics, diet and age all playing a role.

Known surgical techniques for treating damaged cartilage comprise lavage and debridement (joint is flushed with fluid and damaged tissue removed providing temporary symptom relief); microfracture (penetration of the subchondral bone to stimulate bleeding in to the cartilage lesion in an effort to promote a fibrocartilage healing response); periosteal grafts (autologous periosteum is grafted into the defect site and sutured or glued into place); mosaicplasty (plugs of cartilage and bone are harvested from low weight bearing regions of the joint and transplanted into the defect); and autologous chondrocyte implantation (ACI) (cells are isolated and expanded from a cartilage biopsy from a non-weight bearing location, and the cells are re-introduced into the defect in a second procedure approximately six weeks later either in suspension or on a scaffold (Matrix-guided ACI-MACI)).

SUMMARY

The tissue harvesting techniques described below can be used to repair, regenerate, and/or augment tissue in a range of surgical or cosmetic applications.

Trauma to the articular surface is a common injury in sports. The symptoms arising from such damage comprise pain, joint locking, instability, and stiffness, and the damage predisposes the cartilage and joint to wear and degeneration which can lead to osteoarthritis and the need for total knee replacement. For example, the tissue harvesting techniques can be used to treat focal and degenerative cartilage lesions before a total joint replacement is indicated and can postpone or obviate the need for a total joint replacement. The techniques enable the surgical team to purify a unique population of repair cells from tissue from the patient, such as, for example, synovial/adipose tissue, and deliver the cells back into the patient's joint to stimulate a hyaline-like cartilage repair in a single surgical procedure. The repair cells are harvested arthroscopically from a site local to the defect (i.e. within the joint), the repair cells of a desired range are isolated, for example, by filtering, and the isolated cells are mixed in an unprocessed state (e.g., without further culturing, concentrating, etc.) with a biocompatible gel. The mixture of gel and the isolated harvested cells is then provided to the repair site.

In implementations of the disclosure the adipose tissue harvested is a fat pad or corpus adiposum, which is a localised accumulation of encapsulated adipose tissue. Fat pads can be found, for example in the cheek (corpus adiposum buccae) and also found within certain joints where they are referred to as the infrapatellar, navicular, olecranon, scaphoid, pronator quadratus, and preachilles fat pads. These pads may act as a cushion to absorb forces generated across the joint and also may help to distribute lubricants in the joint cavity.

The infrapatellar fat pad, also referred to as Hoffa's pad and adipose synovium, comprises synovium and subsynovial adipose tissues and lies beneath the patella (kneecap) separating it from the femoral condyle. The infrapatellar fat pad varies in size and volume, but generally comprises two large basal prominences lying on either side of the intrachondylar notch. In situations where forces are directed at the patella, the infrapatellar fat pad acts as a shock absorber, protecting the underlying structures. During trauma the infrapatellar fat pad undergoes a number of changes, which comprise, without limitation, the fat pad volume increasing secondary to oedema and haemorrhage due to increased subsynovial vascularisation and the subsequent infiltration of the fat pad with macrophages.

We have found that by harvesting a defined size fragment of fat pad tissue, comprising progenitor cells, and reintroducing this fragment in combination with a biocompatible scaffold, such as a gel, into another site within the body, it is possible to generate tissue types that are different from the tissue fragment following exposure of the fragment to environmental factors.

It is envisaged that the progenitor cells contained within the fragments of fat pad could be directed along, for instance, the osteogenic, adipogenic, chondrogenic, myogenic, neurogenic lineages giving rise to bone, cartilage, muscle or nerve tissue.

Once the fat pad fragments are implanted into the site, the progenitor cells migrate out of the fragments and integrate into the surrounding tissue, thereby allowing the progenitor cells to differentiate into the appropriate endogenous cell type(s).

The fat pad tissue can be autogeneic tissue, allogeneic tissue, xenogeneic tissue and combinations thereof.

The use of autogeneic tissue is particularly desirable as it substantially reduces the potential for an immunogenic host response and tissue rejection.

If autogenic fat pad is to be used, a specific consideration for the surgeon is how readily accessible the fat pad is during the primary surgical procedure. For example, if a surgeon is repairing a cartilage defect within the femoral plateau, then it would be appropriate to use the infrapatellar fat pad. This will minimise the incisions that the surgeon has to make and therefore improve the outcome and the welfare of patient.

Using autologous tissue as a source for cartilage repair implants is often limited due to a number of problems including: availability, source, pain and enrichment. The infrapatellar fat pad is a joint tissue that is easily accessible to the orthopedic surgeon and is present in sufficient quantity to load a number of scaffolds for use in cartilage repair, particularly of focal defects. Furthermore, the use of the infrapatellar fat pad substantially reduces the possibility of secondary site morbidity when compared to other tissue sources, such as bone marrow aspirations, and substantially reduces the need to enrich the progenitor cells to show therapeutic effect.

In one aspect, the present disclosure relates to an apparatus for tissue collection comprising:
a housing defining an inlet and an outlet;
a first filter disposed within the housing;
a second filter disposed within the housing, the second filter configured to isolate tissue particles of a desired size that pass through the first filter under the application of an aspiration force applied through the housing.

Implementations may comprise one or more of the following features. For example, the apparatus further comprises a third filter disposed in the housing between the first and second filters. The second filter is configured to isolate tissue particles of a desired size that pass through the first and third filters under the application of the aspiration force applied through the housing. The first and second filters disposed within the housing define an interior space within the housing, wherein the apparatus further comprises a port disposed within the housing and in fluid-flow communication with the interior space defined within the housing. The apparatus further comprises an introducer configured to comprise a gel. The introducer is configured to be coupled to the outlet of the housing to introduce the gel into the interior space of the housing, such that in use, the gel passes through the second filter and removes isolated tissue particles collected on the second filter, and wherein the gel and isolated tissue particles collect in the interior space of the housing. The apparatus further comprises a mixer and a receiver. The mixer and the receiver are configured to be releasably coupled to the port to receive the gel and isolated tissue particles from the interior space of the housing. The first filter comprises a set of pores having a pore size of about 0.6 mm to about 2.4 mm, the second filter comprises a set of pores having a pore size of about 0.5 mm to about 50 µm, and the third filter comprises a set of pores having a pore size of about 0.6 mm to about 1 mm. The apparatus further comprises a fluid-flow conduit in the interior space of the housing and in fluid-flow communication with the inlet and the outlet. The apparatus further comprises a second port disposed in the housing. The first port and the second port are in fluid-flow communication with the conduit. The apparatus further comprises a first valve and a second valve, the first and second valves configured to allow for selective control of fluid flow between the inlet and the outlet and the first and second ports. The inlet is in fluid communication with a surgical blade and the outlet is in fluid communication with an aspiration source.

In an embodiment, the housing comprises a removable lid. The first filter is disposed within the lid. The third filter is disposed within the lid between the first filter and the second filter. The second filter comprises a basket mesh or a substantially frusto-conical configuration. The second filter is releasably coupled to the housing or the lid. The apparatus further comprises a container shaped to receive the second filter therein upon removal of the second filter from the housing.

In another aspect, the present disclosure relates to a method of harvesting tissue comprising isolating particles of a desired range from cut tissue aspirated through a tissue cutter, mixing the isolated particles in an unprocessed state with a biocompatible gel, and collecting the mixed particles and gel in an introducer for implantation into a surgical site.

Implementations may comprise one or more of the following features. For example, isolating the particles of a desired range comprises passing the cut tissue through a first filter and a second filter. The second filter comprises openings sized to permit collection of the particles of the desired range on the second filter. The method further comprises passing the biocompatible gel through the second filter to remove isolated particles collected on the second filter prior to mixing the isolated particles with the biocompatible gel. Mixing the isolated particles and the gel comprises passing the isolated particles and gel through a mixer coupled to the introducer Mixing the isolated particles and the gel also comprises placing the second filter with the collected particles in a container configured to receive the second filter therein and introducing the biocompatible gel into the container. The collecting step comprises aspirating the mixed isolated particles and the gel from the container into the introducer. The cut tissue is synovial or adipose tissue. The isolating step comprises collecting particles of the desired range in a filter of a tissue collection device solely under the application of an aspiration force applied through the tissue collection device to the aspiration lumen of the tissue cutter to aspirate tissue therethrough.

Advantages may comprise eliminating the risk of disease transmission and immune response associated with treatment using allograft; enabling cartilage repair procedures to be performed in focal lesions in older as well as young patients; minimizing damage to the donor site; isolating tissue fragments which are within a specific size range; minimizing intervention from the surgeon; and harvesting tissue, loading tissue within a gel in an expedient manner, and providing the tissue-containing gel for tissue repair in a sterile manner in a single surgical procedure.

The details of one or more embodiments of the disclosure are set forth in the accompanying drawings and the description below. Other features, objects, and advantages of the disclosure will be apparent from the description and drawings, and from the claims.

DETAILED DESCRIPTION

Figure 1:
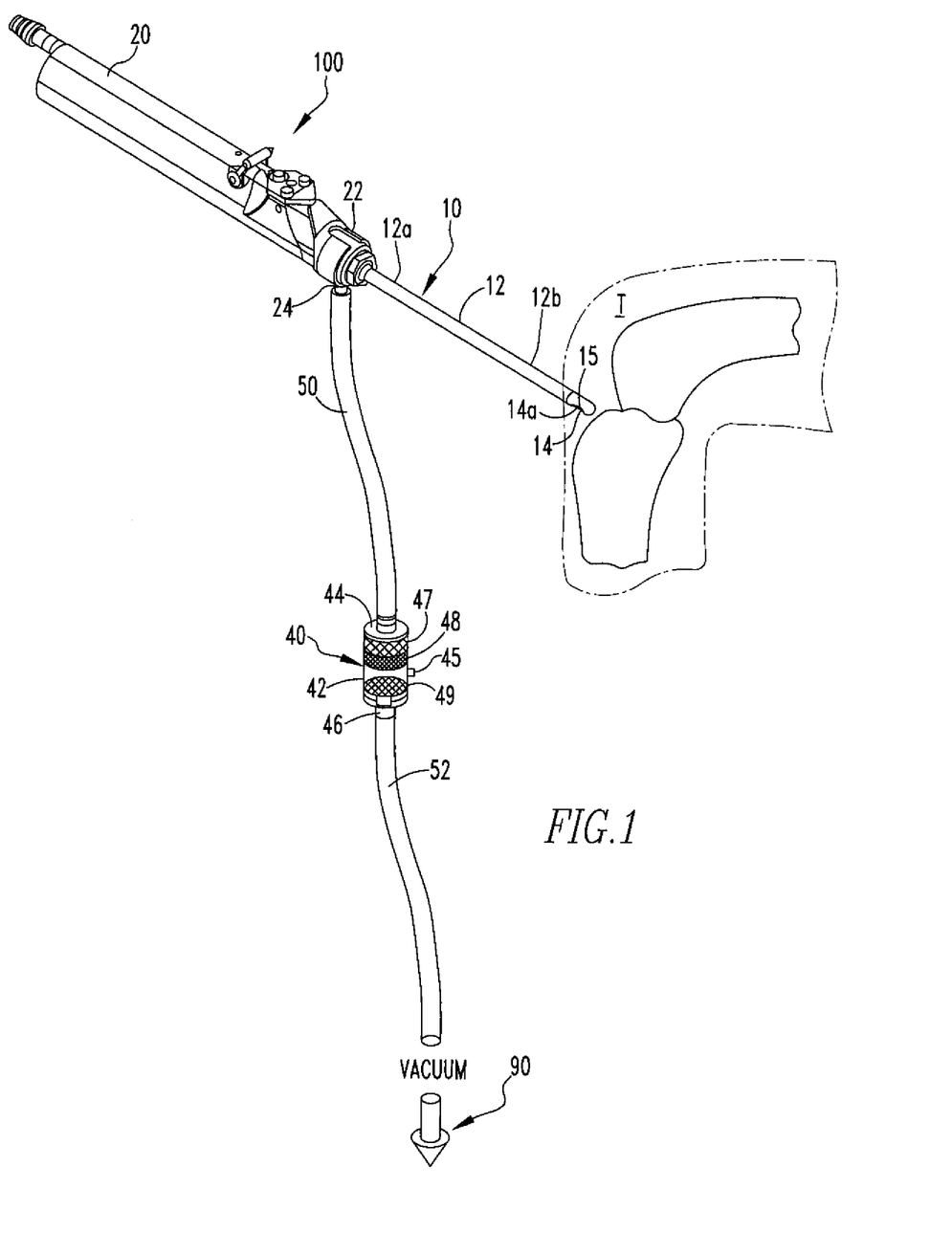
FIG. 1 is an illustration of a tissue harvesting assembly shown in use.

Referring to FIG. 1, a tissue harvesting assembly 100 comprises a surgical blade 10 used to cut or resect bodily tissue T, such as synovial or adipose tissue, from a donor site, coupled to a tissue collection device 40 for isolating cut tissue of a desired size aspirated through the surgical blade 10. As discussed below, during the same surgical procedure, the isolated cut tissue is loaded into, or mixed with, an appropriate carrier, such as a biocompatible gel, and introduced at a tissue repair site. Preferably, the donor site and the repair site are within the same joint to minimize trauma to the patient and provide for a more expedient surgical procedure.

Surgical blade 10 uses a tube-in-tube construction to shear tissue disposed between cutting edges of an elongate outer non-rotating tubular member 12 and an elongate inner rotating tubular member 14, as more fully explained in U.S. Pat. No. 5,871,493, which is incorporated herein by reference in its entirety. The surgical blade 10 comprises a handpiece 20 coupled to the tubular members 12, 14 via a hub 22. The outer tubular member 12 has a proximal end 12a fixed to the hub 22 and a distal end 12b defining an opening 15 forming a cutting port or window. The inner tubular member 14 is rotatably received in the outer tubular member 12 and has a distal end 14a with a cutting edge (not shown). The inner tubular member 14 defines an aspiration lumen 16 (FIG. 2) communicating with the cutting edge to remove cut tissue and fluid from a surgical site. When the blade 10 is assembled, the cutting edge of the inner tubular member 14 is positioned adjacent the opening 15 of the outer tubular member 12.

Figure 2:
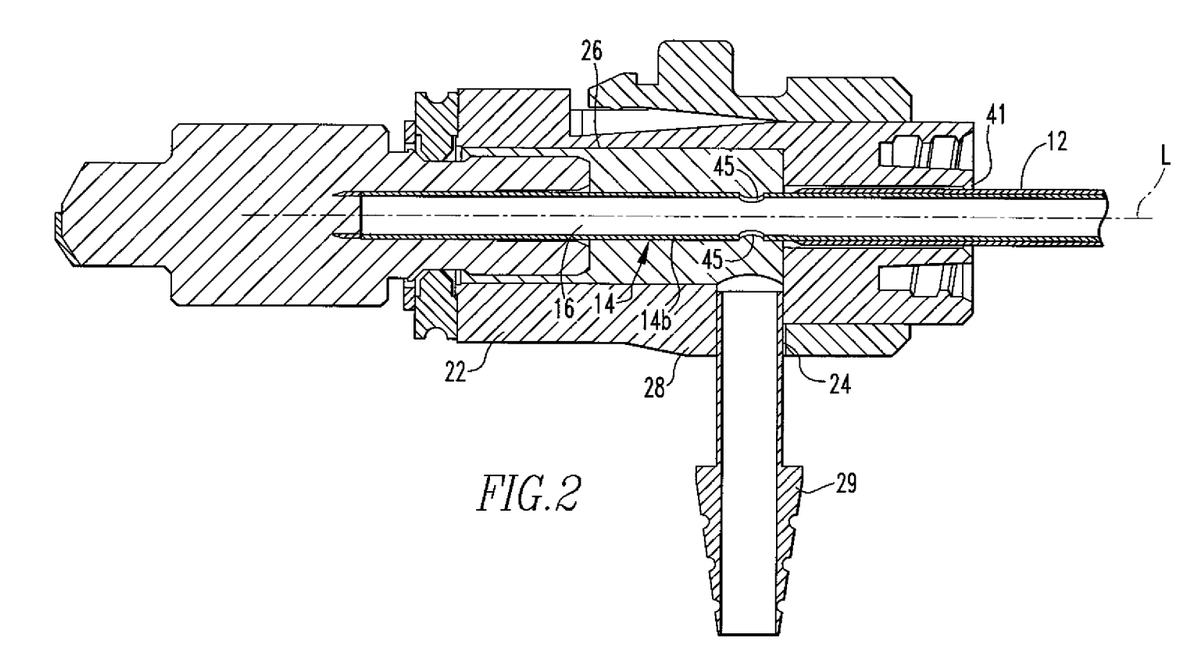
FIG. 2 is a cross-sectional view of the surgical blade hub of the assembly of FIG. 1.

Referring to FIG. 2, the hub 22 (FIG. 1) of the surgical blade 10 is coupled to the outer tubular member 12 via an opening 41 formed in the hub 22. The inner tubular member 14 is rotatably received within the outer tubular member 12 and defines the aspiration lumen 16 extending longitudinally through the inner tubular member 14. The inner tubular member 14 further defines one or more openings 45 formed through a side wall 14b of the member 14 within the hub region of the blade 10, which are in fluid communication with the aspiration lumen 16 and a chamber 26 defined within hub 22. Hub 22 further comprises a side port 24 formed through a side wall 28 of hub 22 and in fluid communication with the chamber 26. The side port 24 extends in a direction substantially transverse to the longitudinal axis L of the inner tubular member 14. Coupled to the side port 24 is a tubing connector 29. The side port 24 provides a pathway for fluid and cut tissue to flow from the surgical blade 10 to the tissue collection device 40.

Figure 3:
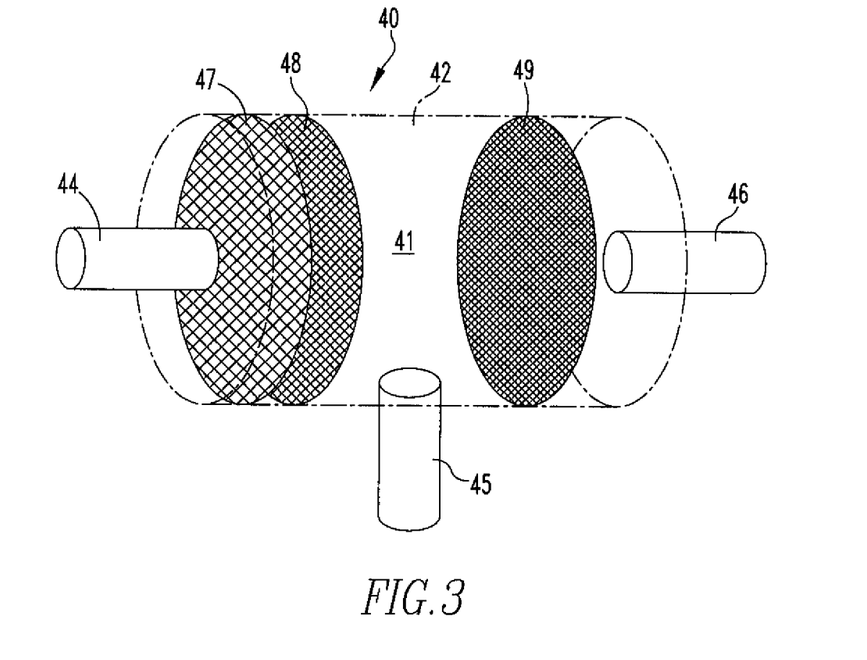
FIG. 3 is a perspective view of a tissue collection apparatus of the assembly of FIG. 1.
Figure 4A:
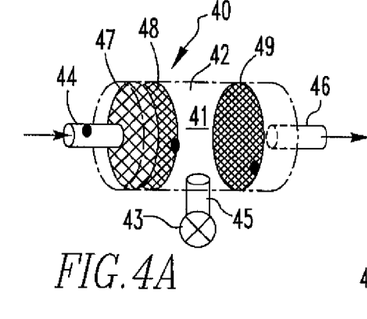
FIGS. 4a-4d schematically illustrate use of the tissue collection apparatus of FIG. 3 to isolate tissue particles of a desired size and to prepare a mixture of tissue-containing gel for tissue repair.
Figure 4B:
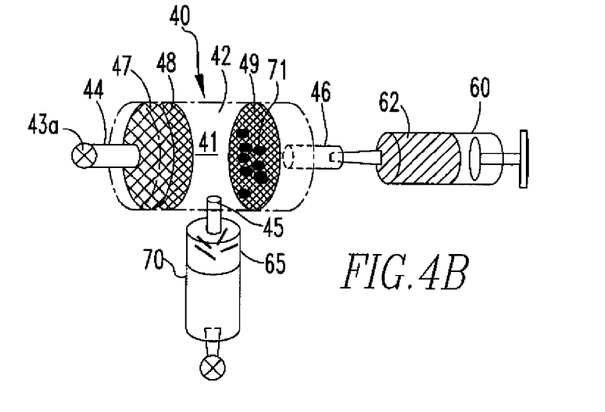
Figure 4C:
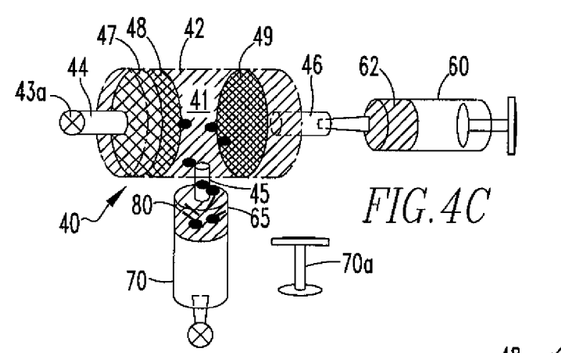
Figure 4D:
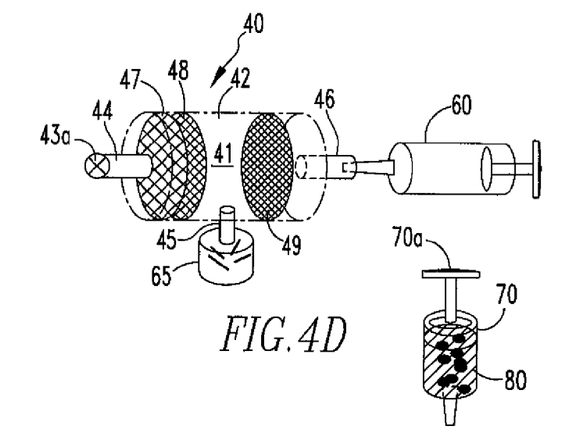

Referring to FIGS. 1, 3, and 4A-4D, in addition to the tissue collection device 40, the tissue harvesting assembly 100 comprises an introducer 60 (FIGS. 4B-4D) and a mixer 65 (FIGS. 4B-4D). The tissue collection device 40 is coupled to the blade 10 via a flexible tubing 50. The tissue collection device 40 comprises a substantially cylindrical housing 42 having an inlet 44 and an outlet 46. The inlet 44 couples the tubing 50 to the tissue collection device 40. The outlet 46 is provided to couple the tissue collection device 40 to a source of vacuum 90 (FIG. 1), such as a vacuum pump or other suitable apparatus for providing aspiration during the surgical procedure, via a tubing 52. In addition, a collection apparatus (not shown) can be coupled to the tissue collection device 40 via the tubing 52 to collect tissue and fluid that passes through the tissue collection device 40.

Filtration devices, such as disc filters 47, 48, and 49, are positioned within the housing 42 with filter 47 disposed closest to or adjacent the inlet 44, filter 49 disposed closest to or adjacent the outlet 46, and filter 48 disposed between filters 47 and 49. The filters 47, 48, and 49 and the housing 42 cooperate to define an interior space 41 within the housing 42. The housing 42 comprises a port 45 disposed therein, which is in fluid-flow communication with the interior space 41 of the housing 42.

In the implementation shown in FIGS. 1, 3, and 4A-4D, the filter 47 comprises a set of pores having a pore size of about 0.6 mm to about 2.4 mm, the filter 48 comprises a set of pores having a pore size of about 0.6 mm to about 1 mm, and the filter 49 comprises a set of pores having a pore size of about 0.5 mm to about 50 µm. The filters 47 and 48 filter out larger tissue particles and allow smaller particles to pass through. The filter 49 then filters out particles 71 (FIG. 4B) of a desired size and allow particles smaller than the desired size to pass through. While two filters 47, 48 are shown in this implementation, the tissue collection device 40 may comprise only one of the filters 47, 48 used in conjunction with the filter 49 to collect tissue particles 71 of a desired size.

The introducer 60 (FIGS. 4B-4D), for example, a syringe, contains a suitable volume (e.g., about 1 ml) of a biocompatible gel 62. After particle collection, the syringe 60 is used to inject the biocompatible gel 62 into the housing 42 to allow the recovery of the tissue particles 71 collected by the filter 49 as will be discussed in more detail below. The mixer 65 (FIGS. 4B-4D), such as a static mixer, is releasably coupled to the port 45 to receive the gel 62 and isolated tissue particles 71 from the interior space 41 of the housing and to create a mixture 80 of gel 62 and tissue particles 71. A receiver 70 (FIGS. 4B-4D) is releasably coupled to the mixer 65 to receive the mixture 80 from the mixer 65 and to, for example, provide the mixture 80 to a surgical site.

In operation, as shown in FIGS. 1 and 4A-4D, the surgical blade 10 is brought into contact with a desired bodily tissue, such as synovial or adipose tissue (FIG. 1). The operator cuts a desired amount of tissue from the donor site using the blade 10. The vacuum source 90 aspirates fluid and the cut tissue through the aspiration lumen 16 of the inner tubular member 14 to the tissue collection device 40. During aspiration of the fluid and cut tissue, the port 45 in the housing 42 is closed (FIG. 4A), using, for example, a valve, stop, plug, or other suitable device 43. The filter 47 removes undesirable cut tissue from the fluid pathway, such as particles larger than, for example, about 0.6 mm to about 2.4 mm. After passing through the filter 47, the remainder of the fluid and cut tissue pass through the filter 48, which removes undesirable cut tissue from the fluid pathway, such as particles larger than, for example, about 0.6 mm to about 1 mm. The remainder of the fluid and cut tissue pass through the filter 49 where tissue particles 71 of a desired size, such as particles larger than, for example, about 0.5 mm to about 50 µm are isolated and/or retained on the filter 49. The remainder of the cut tissue and fluid volume pass through the tissue collection device 40 and are aspirated to the collection apparatus (not shown).

Following aspiration of the fluid and cut tissue, the inlet 44 of the housing 42 is closed off using, for example, a valve, stop, plug, or other suitable device 43a, the housing 40 is removed from the tubing 50, 52, and the receiver 70 and static mixer 65 are attached to the port 45, using, for example, a Luer Lock (not shown) or other suitable connector (FIG. 4B). The syringe 60 containing the gel 62 is coupled to the outlet 46, for example, by a Luer lock (not shown) or other suitable connection. The gel 62 is then injected into the housing 40 and through the filter 49 to mix with and expel the tissue particles 71 from the filter 49 (FIG. 4C). The expelled tissue particles 71 and the gel 62 pass through the interior space 41 of the housing 42 and are forced through the port 45 to the mixer 65 (FIG. 4C). The mixer 65 mixes the tissue particles 71 and the gel 62 to promote even distribution of the tissue particles 71 within the gel 62, creating a mixture 80, which flows into the syringe 70 (FIGS. 4C-4D). Once the desired volume of the mixture 80 is collected in the syringe 70, the operator removes the syringe 70 from the mixer 65 and attaches the plunger 70a of the syringe 70 (FIGS. 4c-d). The operator then applies the mixture 80 at a desired location, such as the surgical site shown in FIG. 1, or the mixture 80 can be placed onto a tissue scaffold or used for further processing.

An alternative implementation of a tissue harvesting assembly 200 is illustrated in FIGS. 5, 6, and 7A-7F. The tissue harvesting assembly 200 comprises a tissue collection device 140 and an introducer 160 (FIGS. 7E-7F), for example, a syringe, containing a suitable volume (e.g., about 1 ml) of gel 62. The tissue collection device 140 comprises a substantially cylindrical housing 142 having an inlet 44 and an outlet 46. The housing 142 comprises a lid 143 that is releasably coupled to the housing 142 using, for example mating threads (not shown), a friction fit, or other suitable connection.

Filtration devices, such as disc filters 147, 148 and a filter 149 having a substantially frusto-conical or basket configuration, are positioned within the housing 142, with filter 147 disposed closest to or adjacent the inlet 44, filter 149 disposed closest to or adjacent the outlet 46, and filter 148 disposed between filters 147 and 149. In particular, the filters 147, 148 are disposed within the lid 143, and the filter 149 is removably attached to an underside 143a of the lid 143, using, for example, threads (not shown), a friction fit, or other suitable connection. The housing 140 comprises one or more projecting ribs 145 (FIG. 6) disposed about the interior of the cylindrical housing 140. The ribs 145 are configured and shaped to receive the filter 149 and to releasably hold the filter 149, for example, by a friction fit, within the housing 140.

The filter 147 comprises a set of pores having a pore size of about 0.6 mm to about 2.4 mm, the filter 148 comprises a set of pores having a pore size of about 0.6 mm to about 1 mm, and the filter 149 comprises a set of pores having a pore size of about 0.5 mm to about 50 µm. The filters 147 and 148 filter out larger tissue particles and allow smaller particles to pass through. The filter 149 then filters out particles 71 (FIG. 7B) of a desired size and allow particles smaller than the desired size to pass through. While two filters 147, 148 are shown, the tissue collection device 140 may comprise only one of the filters 147, 148 used in conjunction with the filter 149 to collect tissue particles 71 of a desired size.

The assembly 200 further comprises a container 170 defining a cavity 170a (FIGS. 7C-7F) configured and shaped to receive the filter 149 in a fluid-tight manner therein. An upper portion 170b of the container 170 is configured with threads, or other suitable mating connections, to receive the lid 143 of the housing 140 as will be described in more detail below.

The introducer 160 (FIGS. 7E-7F), for example, a syringe, contains a suitable volume (e.g., about 1 ml) of gel 62. The syringe 160 is used to mix the gel 62 with the tissue particles 71 to create a mixture 80 within the container 170, and thereafter, to aspirate the mixture 80 from the container 170.

Figure 5:
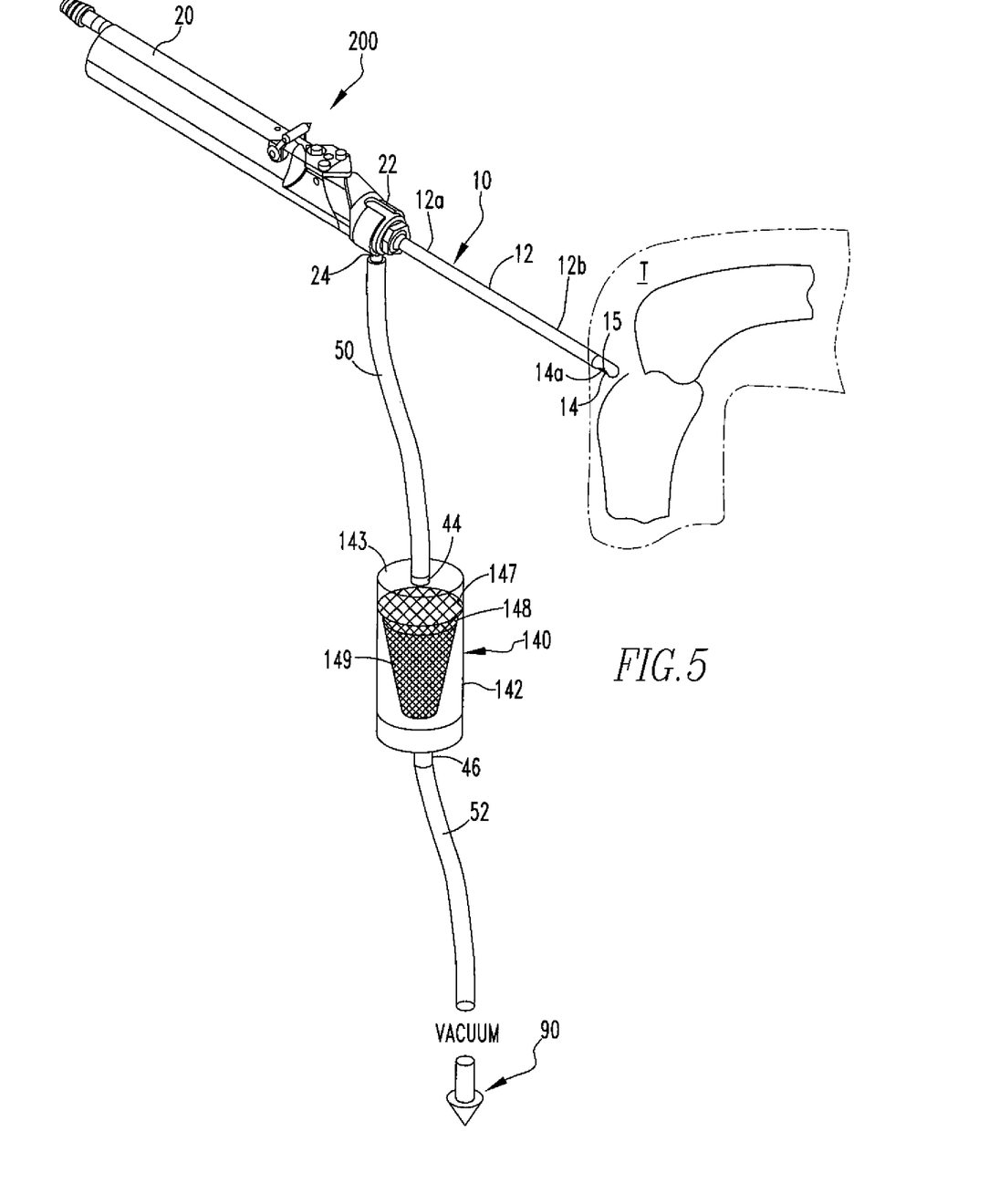
FIG. 5 is an illustration of an alternative tissue harvesting assembly shown in use.
Figure 6:
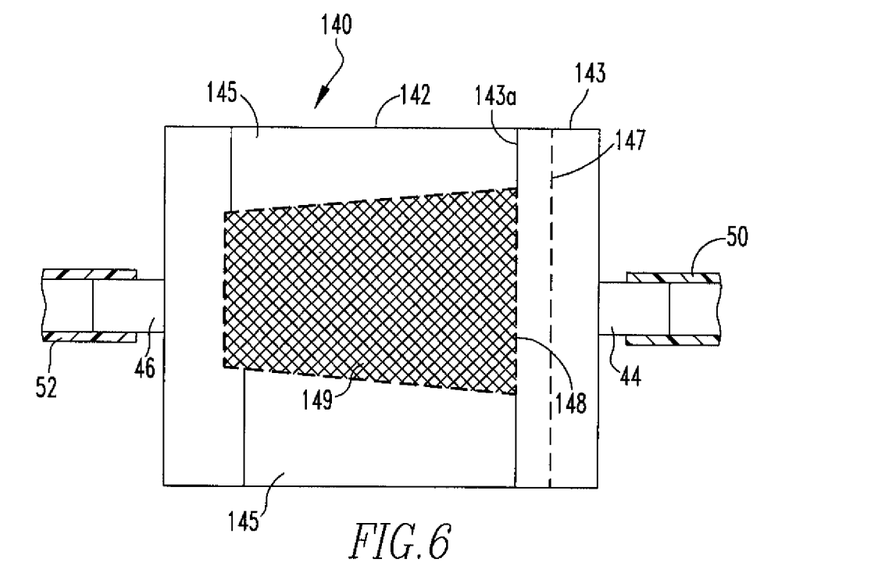
FIG. 6 is a cross-sectional view of a tissue collection apparatus of the assembly of FIG. 5.

In operation, as shown in FIGS. 5 and 7A-7F, the surgical blade 10 is brought into contact with a desired bodily tissue, such as synovial or adipose tissue (FIG. 5). The operator cuts a desired amount of tissue from the donor site using the blade 10. The vacuum source 90 aspirates fluid and the cut tissue through the aspiration lumen 16 of the inner tubular member 14 to the tissue collection device 140. During aspiration, the fluid and cut tissue flow through the filter 147, which removes undesirable cut tissue from the fluid pathway, such as particles larger than, for example, about 0.6 mm to about 2.4 mm. After passing through the filter 147, the remainder of the fluid and cut tissue pass through the filter 148, which removes undesirable cut tissue from the fluid pathway, such as particles larger than, for example, about 0.6 mm to about 1 mm. The remainder of the fluid and cut tissue pass through the filter 149 where tissue particles 71 (FIG. 7B) of a desired size, such as particles larger than, for example, about 0.5 mm to about 50 µm are isolated and/or retained on the filter 149. The remainder of the cut tissue and fluid volume pass through the tissue collection device 140 and are aspirated to the collection apparatus (not shown).

Figures 7A, 7D:
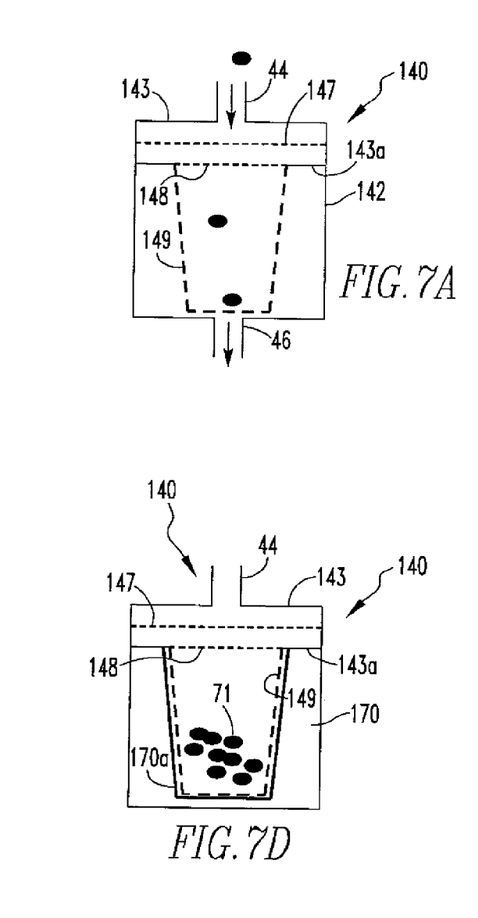
FIGS. 7a-7f schematically illustrate use of the tissue collection apparatus of FIG. 6 to isolate tissue particles of a desired size and to prepare a mixture of tissue-containing gel for tissue repair.
Figure 7B:
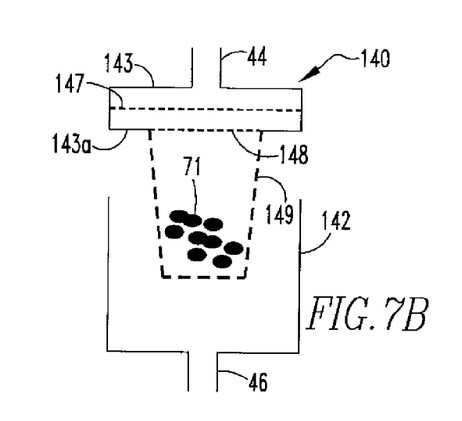
Figure 7C:
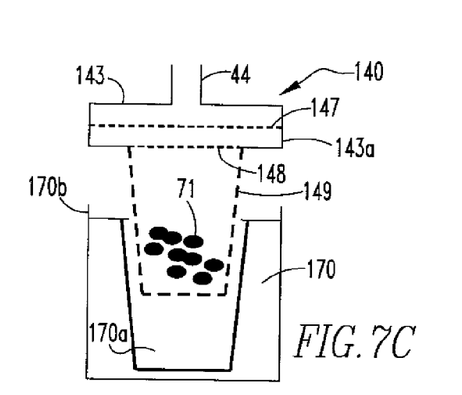

Following aspiration of the fluid and cut tissue, the lid 143, including the filters 147, 148, and 149, is removed from the housing 142 (FIG. 7B) and coupled to the upper portion 170b of the container 170 (FIG. 7C-7D). The cavity 170a receives the filter 149 in a fluid-tight manner, via, for example, a friction fit, between the filter 149 and the cavity 170a. Once the filter 149 is positioned in the container 170, the operator removes the lid 143, including the filters 147, 148, from the container 170, leaving the filter 149 within the cavity 170a of the container 170. For example, if the filter 149 is coupled to the lid 143, using a threaded connection and the lid 143 is coupled to the container 170 via a threaded connection, the two sets of threaded connections may be configured such that when the lid 143 is unscrewed from the container 170, the filter 149 is unscrewed from the lid 143. Alternatively, if, for example, the filter 149 is coupled to the lid 143 via a friction fit, then the cavity 170a of the container 170 is configured to provide a sufficient force to retain the filter 149 upon removal of the lid 143 from the container.

Figure 7E:
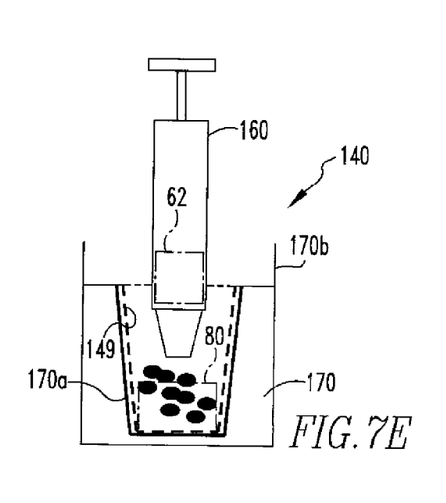
Figure 7F:
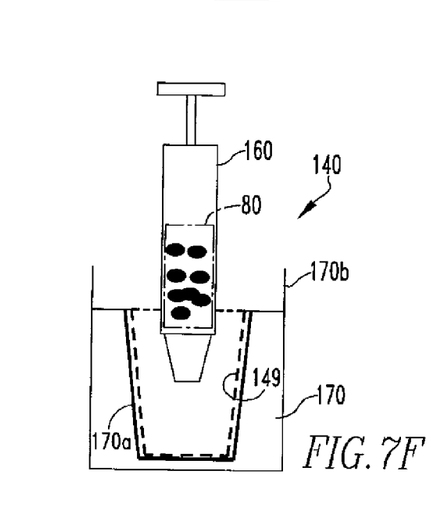

Once the lid 143 is removed from the container 170, the operator uses the syringe 160 to inject the gel 62 within the cavity 170a. The gel 62 mixes with the tissue particles 71 to form a mixture 80 of tissue and gel (FIG. 7E). The mixture 80 is then aspirated from the container 170 using the syringe 160 (FIG. 7F). Once the desired volume of the mixture 80 is collected in the syringe 160, the operator may apply the mixture 80 at a desired location, such as the surgical site shown in FIG. 5, or the mixture 80 can be placed onto a tissue scaffold or used as a feed for further processing.

Figure 8:
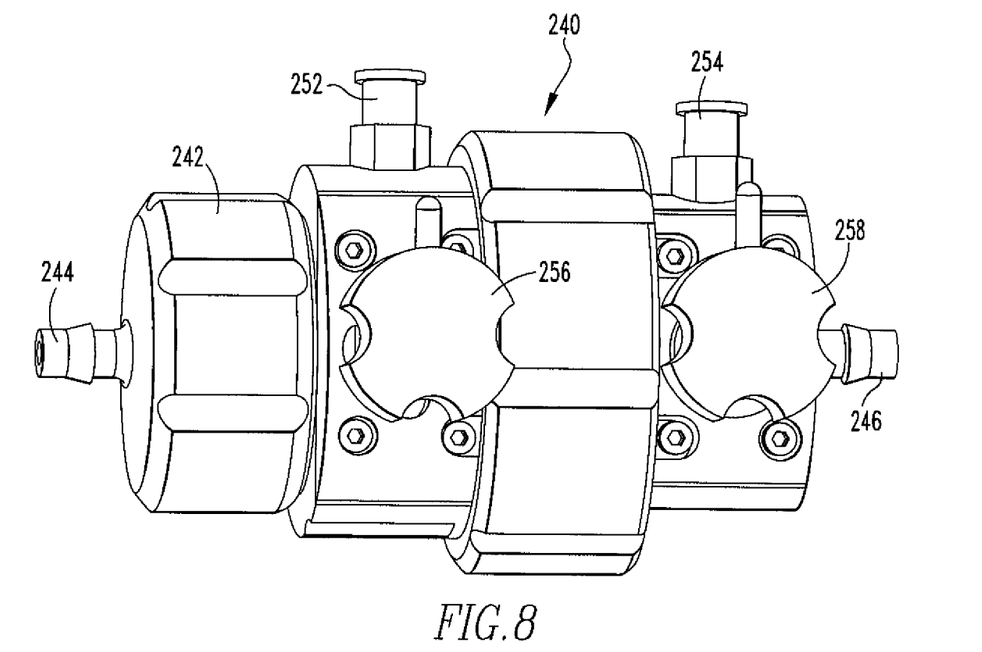
FIG. 8 is an illustration of an alternative implementation of the tissue collection apparatus of the assembly of FIG. 1.
Figure 9:
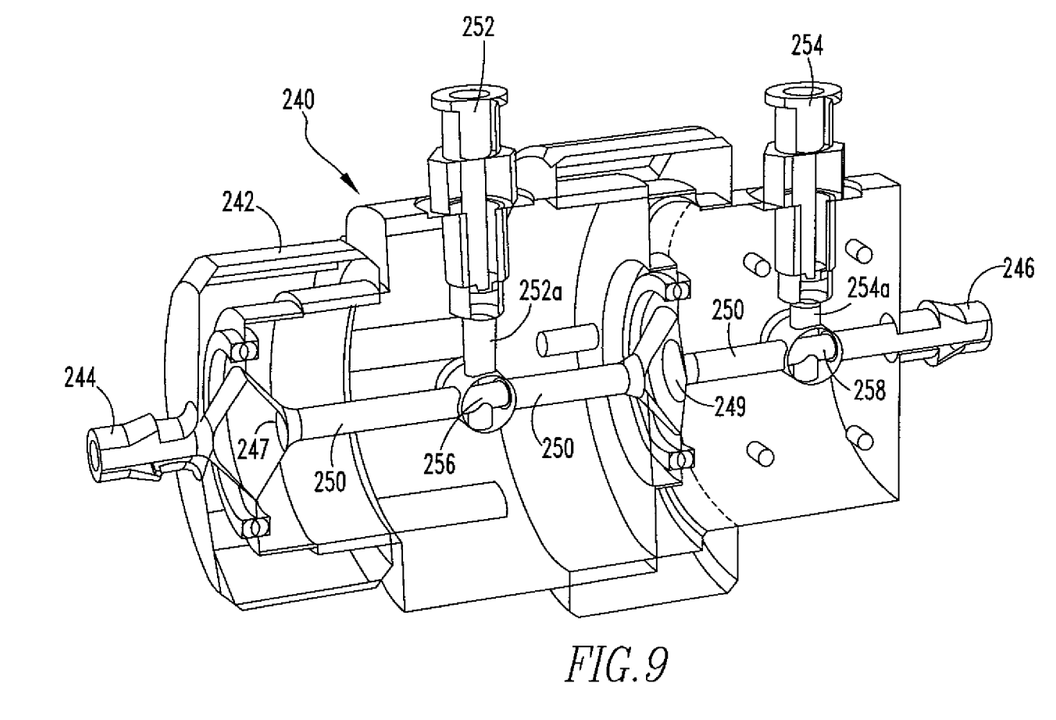
FIG. 9 is a cross-section view of the tissue collection apparatus of FIG. 8.

In an alternative implementation illustrated in FIGS. 8 and 9, a tissue collection device 240 comprises a housing 242 having an inlet 244 and an outlet 246. Positioned within the housing 242 are filters 247 and 249. Filter 247 is disposed adjacent the inlet 244 and filter 249 is disposed adjacent the outlet 246. Extending between the inlet 244 and the outlet 246 is a fluid-flow conduit 250 in fluid-flow communication with the inlet 244, the outlet 246 and the filters 247 and 249. The housing 242 further comprises ports 252 and 254 in fluid-flow communication with the conduit 250 via conduits 252a and 254a, respectively. At the intersections of conduits 250 and 252a and conduits 250 and 254a are three-way valves 256, 258, respectively, that control flow of fluid and tissue or cells between the inlet 244 and the outlet 246, and flow of gel and a mixture of gel and tissue or cells between the ports 252 and 254, as will be described in more detail below.

In the implementation shown in FIGS. 8 and 9, the filter 247 comprises a set of pores having a pore size in the range of about 0.6 mm to about 2.4 mm to allow particles smaller than the pore sizes to pass through the filter 247 and the filter 249 comprises a set of pores having a pore size of about 50 µm to about 0.5 mm to capture particles larger than about 50 µm in the filter 249.

In operation, the operator cuts a desired amount of tissue from a donor site using the surgical blade 10, as described above, and fluid and cut tissue are aspirated through the tissue collection device 240 via the inlet 244. During aspiration of the fluid and cut tissue, the ports 252 and 254 are closed to fluid flow by the three-way valves 256 and 258. The filter 247 removes undesirable cut tissue from the fluid pathway, such as particles in the range of larger than about 0.6 mm to about 2.4 mm. After passing through the filter 247, the fluid and cut tissue pass through the conduit 250 and through the filter 249 where tissue particles of a desired size, such as particles larger than, for example, about 0.5 mm to about 50 µm are isolated and/or retained on the filter 249. The remainder of the cut tissue and fluid volume pass through the tissue collection device 240 and are aspirated to a collection apparatus (not shown).

Following aspiration of the fluid and cut tissue, the inlet 244 of the housing 242 is closed off to fluid flow and the port 252 is opened to fluid flow using, for example, three-way valve 256. Likewise, the outlet 246 of the housing 242 is closed off to fluid flow and the port 254 is opened to fluid flow using, for example, three-way valve 258. The receiver 70, and optionally, the static mixer 65, discussed above, can then be attached to the port 252. The syringe 60 containing the gel 62 is then coupled to the port 254 and the gel 62 is injected into the housing 240 and through the filter 249 to mix with and expel the tissue particles (not shown) from the filter 249. The expelled tissue particles and gel 62 pass through the conduit 250 and are forced through the port 252 to, for example, the mixer 65 (FIG. 4C) and into the receiver 70 as described above.

In addition to being used in conjunction with the surgical blade assemblies described above, each of the tissue collection devices 40, 140, and 240 can be loaded with biological components by other methods. For example, cell pellets cultured in vitro can be aspirated (e.g. using a vacuum source) through one of the tissue collection devices 40, 140, 240 and then mixed with a biocompatible gel in the manner described above.

A number of implementations of the disclosure have been described. Nevertheless, it will be understood that various modifications may be made without departing from the spirit and scope of the disclosure. For example, while the tissue collection devices 40, 140, 240 have been described as coupled to the blade 10 via a flexible tubing 50, the devices 40, 140, 240 could be directly coupled to, for example, the port 24 of the blade 10 (see FIGS. 1 and 5). In addition, although the tissue collection devices 40, 140, 240 have been described as including substantially cylindrical housings 42, 142, and 242, respectively, housings 42, 142, and 242 could be any suitable shape. Further, although the syringes 60, 160 have been described as containing a volume of about 1 ml of a biocompatible gel 62, the syringes 60, 160 could contain more or less of the gel 62 depending on the size of the defect to be treated.

In addition, rather than using a static mixer with the tissue collection device 40 to promote a more even distribution of the tissue particles 71 in the gel 62, the mixture 80 of gel 62 and tissue particles 71 may be realized solely within the interior space 41 of the housing 42, and the syringe 70 can be directly coupled to the port 45 to recover the mixture 80 directly from the interior space 41 of the housing 42. Further, rather than mixing the gel and tissue in a separate container, such as container 170, the outlet 46 of the tissue collection device 140 can be plugged or otherwise sealed and the mixture 80 of gel 62 and tissue particles 71 can be realized directly in the tissue collective device 140.

Moreover, although the filtration devices have been described as either disk-shaped or basket-shaped filters, other suitable filtration devices having any number of possible geometric shapes may be employed. Such examples comprise nucleated cell, microfiltration, tubular, or hollow fiber filtration devices, having, for example, square, cylindrical, tubular, or round geometries. In addition, any filtration surface that contacts any of the relevant compositions of the tissue, fluid, or other surgical materials is sterile or can be readily sterilized.

For the purposes of this disclosure, the injectable gel 62 may comprise any suitable biological or synthetic gels. For example, the gel can comprise hyaluronic acid, alginate, cross-linked alginate, collagen, fibrin glue, fibrin clot, poly (N-isopropulacrylamide), agarose, chitin, chitosan, cellulose, polysaccharides, poly(oxyalkylene), a copolymer of poly (ethylene oxide)-poly(propylene oxide), poly(vinyl alcohol), polyacrylate, Matrigel, or blends thereof.

The apparatuses and systems described herein may be considered disposable, although they may be reused upon sterilization, such as by gamma irradiation, ethylene oxide, formalin, hydrogen peroxide, or sodium hypochlorite. The filters and syringes discussed herein may be commercially obtained. In particular implementations, the apparatus and components may be plastic, metal, or other suitable material.

Rather than the tubing connector 29 (FIG. 2) being in communication with the aspiration lumen 16 of the inner tubular member 14 via the chamber 26, the tubing connector 29 could be directly coupled to the inner tubular member 14. The tubing connector 29 can be coupled to the side port 24 using any suitable form of connection, including glue, weld, press fit, or, alternatively, the tubing connector 29 can be formed as one piece with the hub 22. The tubing connectors described herein can be made from plastic, metal, or any other suitable materials.

In addition, although the tissue harvesting assembly has been described as including a surgical blade 10 used to cut or resect bodily tissue, such as soft tissue, the tissue harvesting assembly can comprise an apparatus containing a curet or burr, for example, to remove bodily tissue, such as bone tissue.

Accordingly, other embodiments are within the scope of the following claims.

What is claimed is:

1. An apparatus for tissue collection comprising:
a housing defining an inlet, an outlet, and a port located between the inlet and the outlet;
a first filter disposed within the housing;
a second filter disposed within the housing, the second filter configured to isolate tissue particles of a desired size that pass through the first filter under the application of an aspiration force applied through the housing,
wherein the first and second filters disposed within the housing define an interior space within the housing, the port in fluid communication with the interior space, the port including two open ends and coupled to the housing such that a direction of fluid flowing between the open ends is perpendicular to a direction of the aspiration of the tissue through the housing, and
wherein the first filter comprises a plurality of pores having a pore size of 0.6 mm to 2.4 mm and the second filter comprises a plurality of pores having a pore size of 0.5 mm to about 50 μm.

2. The apparatus of claim 1 wherein the apparatus further comprises a third filter disposed in the housing between the first and second filters, the second filter configured to isolate tissue particles of a desired size that pass through the first and third filters under the application of the aspiration force applied through the housing.

3. The apparatus of claim 2, wherein the third filter comprises a plurality of pores having a pore size of 0.6 mm to 1 mm.

4. The apparatus of claim 1 further comprising an introducer configured to comprise a gel and configured to be coupled to the outlet of the housing to introduce the gel into the interior space of the housing, such that in use, the gel passes through the second filter and removes isolated tissue particles collected on the second filter, and wherein the gel and isolated tissue particles collect in the interior space of the housing.

5. The apparatus of claim 4, further comprising a mixer and a receiver, the mixer and the receiver configured to be releasably coupled to the port to receive the gel and isolated tissue particles from the interior space of the housing.

6. The apparatus of claim 1 wherein the inlet is in fluid communication with a surgical blade.

7. The apparatus of claim 1 wherein the outlet is in fluid communication with an aspiration source.

8. The apparatus of claim 1 further comprising a fluid-flow conduit in the interior space of the housing and in fluid-flow communication with the inlet and the outlet.

\* \* \* \* \*